United States Patent [19]

Williams

[11] 4,402,329
[45] Sep. 6, 1983

[54] POSITIVE ANCHORING A-V LEAD

[75] Inventor: Terrell M. Williams, Coon Rapids, Minn.

[73] Assignee: Medtronic, Inc., Minneapolis, Minn.

[21] Appl. No.: 306,050

[22] Filed: Sep. 28, 1981

[51] Int. Cl.³ .............................................. A61N 1/04
[52] U.S. Cl. .................................... 128/785; 128/786; 128/419 P
[58] Field of Search .............................. 128/784–786, 128/419 P

[56] References Cited

U.S. PATENT DOCUMENTS

| 4,026,303 | 5/1977 | Babotai | 128/419 P X |
| 4,057,067 | 11/1977 | Lajos | 128/418 |
| 4,106,512 | 8/1978 | Bisping | 128/418 |
| 4,136,703 | 1/1979 | Wittkempf | 128/419 P |
| 4,289,144 | 9/1981 | Gilman | 128/785 |
| 4,332,259 | 6/1982 | McCorkle, Jr. | 128/786 |

FOREIGN PATENT DOCUMENTS 2605590 8/1977 Fed. Rep. of Germany ... 128/419 P

Primary Examiner—Lee S. Cohen
Attorney, Agent, or Firm—Reed A. Duthler; John L. Rooney; Joseph F. Breimayer

[57] ABSTRACT

A single pass atrial-ventricular transvenous pacing lead wherein the atrial branch has a positive fixation device. The proximal end of the lead has a standard electrical connector for coupling both atrial and ventricular electrodes to an implantable pulse generator. The lead is bifurcated at a point near or above the superior vena cava during normal transvenous insertion. The atrial and ventricular branches are of a fixed length from the point of bifurcation to the distal tip. The ventricular branch preferably employs a passive fixation device such as tines to maintain the ventricular electrode within the right ventricular apex. The atrial branch is positioned in the normal manner under control of a stylet to obtain optimal sensing and stimulation thresholds. This position is maintained using an active fixation device. Preferably the active fixation device is a helix which is screwed into the atrial wall by rotating the atrial connector pin and conductor coil.

15 Claims, 5 Drawing Figures

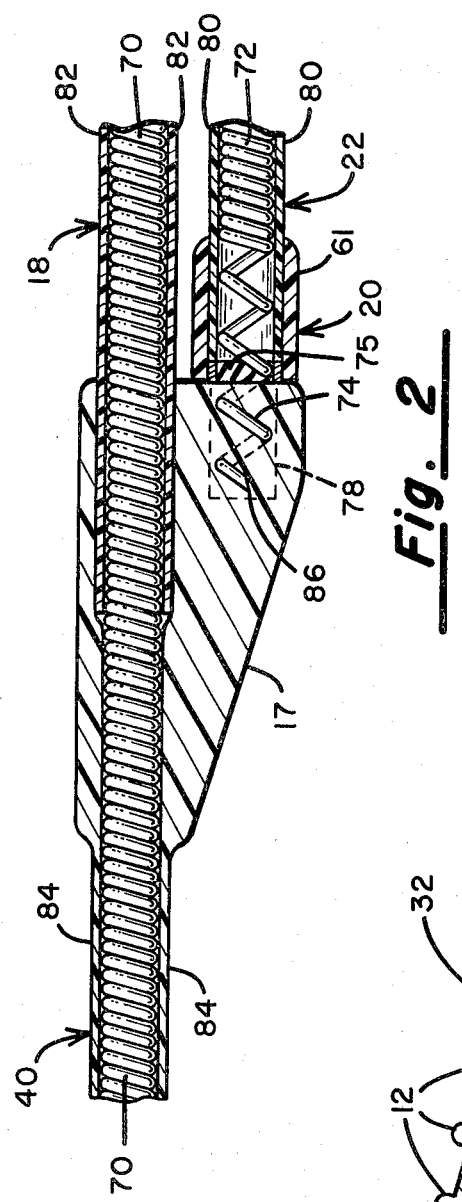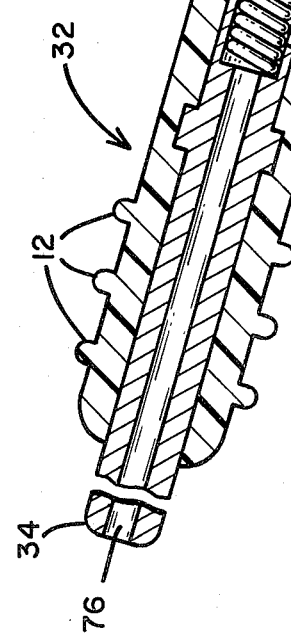

POSITIVE ANCHORING A-V LEAD

CROSS-REFERENCE TO CO-PENDING APPLICATIONS

The reader's attention is directed to the following commonly assigned co-pending U.S. patent applications which are herein incorporated by reference:

(1) Single Pass A-V Lead by Smyth et al., Ser. No. 203,298, filed Nov. 3, 1980;

(2) Screw-In Lead Having Lead Tip with Membrane, by Smits, Ser. No. 192,265, filed Sept. 30, 1980, now U.S. Pat. No. 4,311,153;

(3) Single Pass A-V Leads by Stokes, Ser. No. 230,940, filed Feb. 2, 1981; and (4) "J" Stylet Wire by Dutcher, Ser. No. 244,933, filed Mar. 19, 1981, now U.S. Pat. No. 4,381,013.

BACKGROUND OF THE INVENTION

1. Field of the Invention

The present invention generally relates to implantable medical apparatus and more specifically relates to implantable apparatus for electrical sensing or stimulation of muscle tissue.

2. Description of the Prior Art

The earliest users of transvenous leads for artificial intracardiac pacing produced unacceptable dislodgement rates which yielded substantially increased chronic pacing thresholds. In response thereto, a number of fixation devices have been employed. "Active fixation" which pierces tissue is taught by Bisping in U.S. Pat. No. 4,106,512. Bisping uses a helical fixation coil which is rotated and advanced by rotating the connector pin. In this way the distal end of the pacing lead is screwed into the endothelial tissue and thereby secured.

A second fixation technique is that of "passive fixation" which does not pierce tissue as taught by Citron et al. in U.S. Pat. No. 3,902,501. The use of tines for passive fixation is extremely common in the art.

The leads taught by Bisping and Citron et al. are intended for use in sensing and pacing within a single chamber. However, the current trend has been toward physiological pacing which involves sensing and pacing within both the right atrium and right ventricle. This may be accomplished by passing two separate leads, one for each chamber, using two different veins or even a single vein. A preferred method, however, is the use of a single pass lead which enables the implantation of atrial and ventricular electrodes from a single lead body.

U.S. Pat. No. 4,057,067 issued to Lajos teaches an early single pass lead. The primary difficulty with the Lajos lead is that the atrial and ventricular electrodes are located at a fixed distance from the bifurcation point. This provides difficulty in securing optimal positioning of both electrodes for implantation in hearts of varying size.

The co-pending Smyth et al. and Stokes applications referenced above the assigned to the assignee of the present invention describe techniques for overcoming the problem of varying heart size. Smyth et al teach a "slider" method whereby the interelectrode spacing is adjustable at the time of implant. This approach is effective, but requires establishing a tight seal at the point of bifurcation and cutting off the excess conductor length in the operating room.

Stokes teaches a method of achieving a similar result by letting the excess conductor length be stored chronically within the atrium. This technique requires storage of a great deal of excess conductor with a possible diminishing of hemodynamic efficiency.

SUMMARY OF THE INVENTION

The present invention employs a single pass lead having fixed interelectrode spacing. This results from having the atrial and ventricular branches fixed rather than slideably coupled at the point of bifurcation. The lengths of the atrial and ventricular branches are such as to afford optimal electrode placement when the bifurcation point is in the superior vena cava of a patient having a grossly enlarged heart. The ventricular branch employs tines for passive fixation. The atrial branch employs an active fixation, screw-in electrode. During implantation the active fixation helix of the atrial branch is secured to a receiver fixedly attached to the ventricular branch permitting easy transvenous passage of the lead.

BRIEF DESCRIPTION OF THE DRAWINGS

FIG. 2 is a side sectional view of the active fixation helix secured to the receiver.

FIG. 3 is a side sectional view of the electrical connector at the proximal end.

DETAILED DESCRIPTION OF THE PREFERRED EMBODIMENT

The present invention is described herein as employed in the preferred embodiment of the inventor. However, those of skill in the art will be readily able to apply this invention to other modes of operation based upon the following description.

Figure 1:
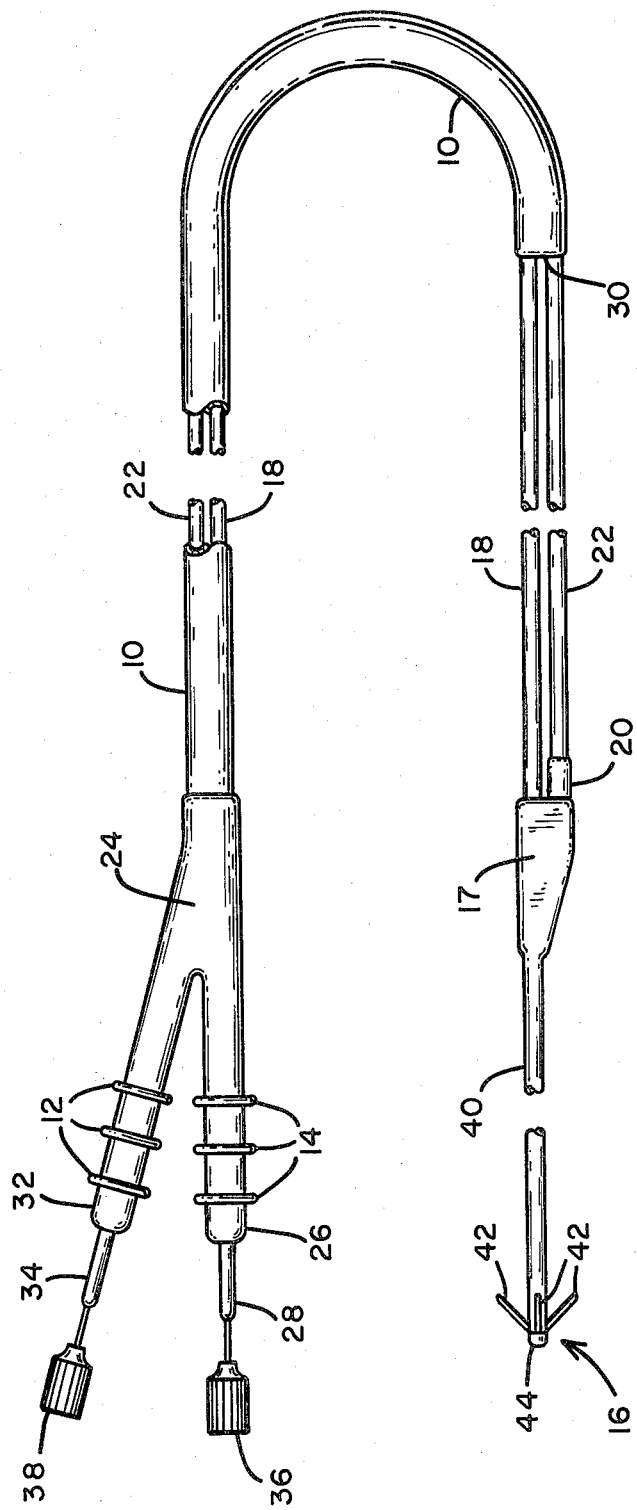
FIG. 1 is a plan view of a single pass atrial-ventricular lead employing the present invention in the preimplant configuration.

FIG. 1 is a plan view of a single pass atrial-ventricular lead in a configuration ready for implant. The proximal end contains electrical bifurcated connector 24 having sealing rings 12 and 14. Connector branch 32 contains metallic terminal pin 34 which is electrically coupled to the atrial electrode via an atrial coiled conductor (not shown). Stylet 38 is inserted into a central lumen of terminal pin 34 and from there through the atrial coiled conductor.

Connector branch 26 contains terminal pin 28 which is electrically coupled to ventricular electrode 44 via a ventricular coiled conductor (not shown). A stylet 36 is inserted into the central lumen of terminal pin 28.

The main body of the lead is covered by insulating sheath 10 of a body compatible material such as urethane or silicone rubber. Sheath 10 covers atrial branch 22 and ventricular branch 18 from connector 24 to bifurcation point 30. Since atrial branch 22 and ventricular branch 18 are each insulated with a body compatible material between connector 24 and the distal tip, it is not necessary to seal bifurcation point 30 against the ingress of all body fluids.

Ventricular branch 18 has receiver 17 located at the same distance from bifurcation point 30 as atrial electrode assembly 20. This permits the active fixation helix (not shown) to secure atrial electrode assembly 20 to receiver 17. The result is that during transvenous insertion, atrial branch 22 is attached to ventricular branch 18 and the entire lead is passed as a single entity.

Distal of receiver 17 is ventricular extension 40 which is also covered by body compatible insulating material. At the distal end of ventricular extension are tines 42 which supply passive fixation as taught in commonly assigned U.S. Pat. No. 3,902,501 issued to Citron et al. At the distal tip of ventricular extension is attached ventricular electrode 44 made of platinum, platinum/iridium or other chronically implantable electrode material.

FIG. 2 is a side sectional closeup of receiver 17 with atrial electrode assembly 20 secured thereto. Atrial electrode assembly 20 contains fixation helix 74, having sharpened tip 86. Fixation helix 74 is attached to atrial conductor coil 72 as shown. Atrial sheath 80 of body compatible insulating material covers atrial conductor coil 72. The proximal end of atrial conductor coil 72 is attached to terminal pin 34 as shown in FIG 3. Rotation of terminal pin 34 causes rotation of atrial conductor coil 72 which, in turn, causes fixation helix 74 to move proximal or distal to the guide seal 75 (see also FIG. 2) at the distal tip of atrial electrode assembly 20. A more detailed explanation of the operation of fixation helix 74 is found in commonly assigned U.S. Pat. No. 4,106,512 issued to Bisping.

Referring again to FIG. 2, it can be seen that fixation helix 74 is screwed into area 78 of receiver 17. For ease of operation, area 78 may be made of a softer, biocompatible material than the remainder of receiver 17 or may have a preformed helical lumen to facilitate securing of fixation helix 74. Ventricular branch 18 contains ventricular conductor coil 70, which is covered by ventricular sheath 82 proximal of receiver 17 and ventricular extension sheath 84 distal of receiver 17. Referring again to FIG. 3, the detail of bifurcated connector 24 can be seen. Lumen 76 of terminal pin 34 and lumen 84 of terminal pin 28 are clearly shown. These are available for the insertion of stylets 38 and 36, respectively (see also FIG. 1). As discussed above, terminal pin 34 is rotatable in either direction. This permits rotation of fixation helix 74 via atrial conductor coil 72. Terminal pin 28, on the other hand, may be fixed and need not rotate, but is electrically coupled to ventricular coiled conductor 70.

Figure 4:
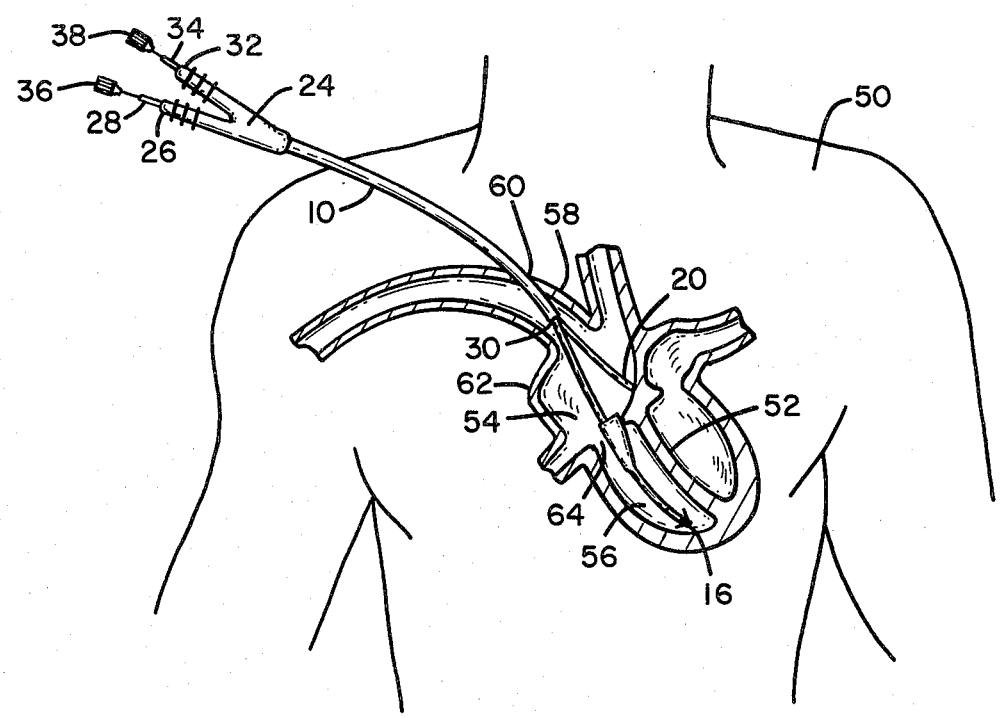
FIG. 4 is a schematic view of a heart during implant.
Figure 5:
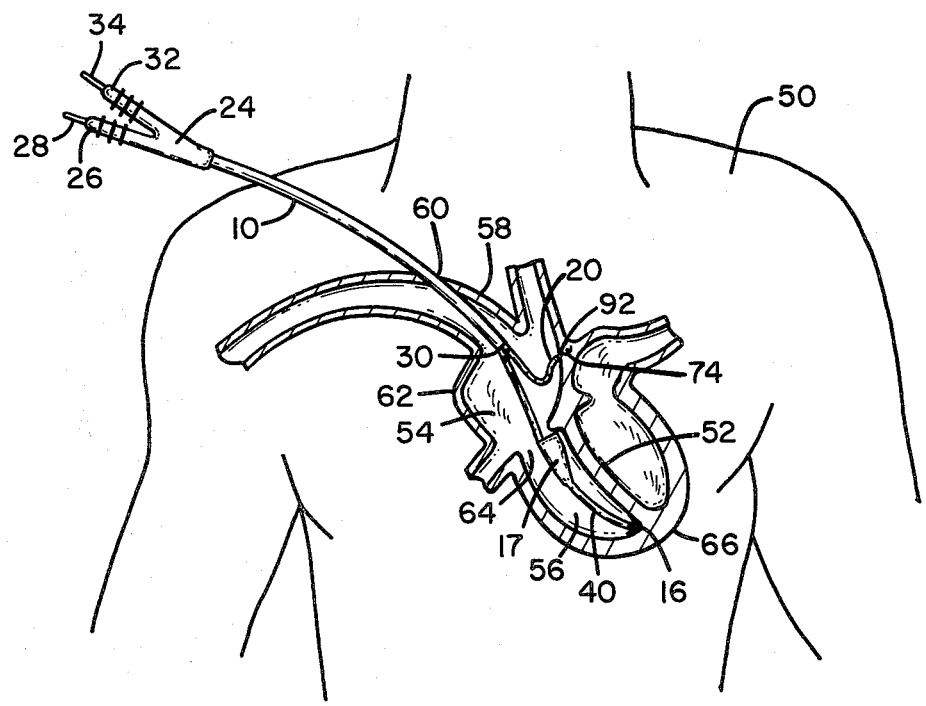
FIG. 5 is a side schematic view of heart after permanent positioning of the atrial and ventricular electrodes.

FIGS. 4 and 5 show implantation of a single pass atrial-ventricular lead employing the present invention into human body 50. A veinotomy 60 is made in peripheral vein 58. The single pass atrial-ventricular lead is inserted, distal end first, into veinotomy 60 with atrial electrode assembly 20 firmly secured in receiver 17 (See also FIG. 1). After the approximate location is reached, terminal pin 34 is rotated in a counter-clockwise direction, retracting fixation helix 74, thereby separating atrial electrode assembly 20 from receiver 17. This yields the configuration shown in FIG. 4. At this point ventricular extension 40 has passed mitral valve 64 locating distal tip 16 within right ventricle 56. Similarly, atrial electrode assembly 20 is located within atrium 54. Bifurcation point 30 is located in the superior vena cava.

Atrial branch 22 and ventricular branch 18 may now be separately and individually manipulated via stylets 38 and 36 to achieve optimal electrode positioning. Positioning of atrial electrode assembly 20 probably involves imparting a "J" shape to stylet 38.

FIG. 5 shows the lead position after both electrodes are properly positioned. Distal tip 16 of ventricular extension 40 is positioned near ventricular apex 66.

Atrial electrode assembly 20 is likely positioned rather high at point 92 of the atrial wall. After positioning, fixation helix 74 is screwed into the tissue of the atrial wall by clockwise rotation of terminal pin 34. Because atrial electrode assembly 20 is firmly attached to the atrial wall via fixation helix 74 and distal tip 16 is securely positioned in right ventricular apex 66, more or less slack may be present in atrial branch 22, ventricular branch 18, or ventricular extension 40 without causing electrode dislodgement.

Having thus described the preferred mode of the present invention, those of ordinary skill in the art will be able to adapt the present invention to configurations using other fixation devices.

What is claimed is:

1. A body implantable lead comprising:
   an atrial conductor having a proximal end and a distal end;
   a ventricular conductor having a proximal end and a distal end;
   an outer insulative sheath covering a portion of said atrial conductor and a portion of said ventricular conductor;
   a ventricular electrode coupled to the distal end of said ventricular conductor;
   a first electrical connector coupled to the proximal end of said ventricular conductor;
   a second electrical connector coupled to the proximal end of said atrial conductor; and
   an atrial electrode assembly coupled to said distal end of said atrial conductor and including means for actively affixing said atrial electrode assembly to body tissue.

2. A body implantable lead according to claim 1 further comprising:
   ventricular affixing means coupled to said distal end of said ventricular conductor for affixing said ventricular electrode to body tissue.

3. A body implantable lead according to claim 2 wherein said atrial conductor is shorter than said ventricular conductor.

4. A body implantable lead according to claim 3 further comprising:
   a receiver means fixedly attached to said ventricular conductor distal to said outer sheath for removably receiving said actively affixing means.

5. A body implantable lead according to claim 4 further comprising:
   a first inner insulative sheath covering said atrial conductor, mounted fixedly with respect to said outer sheath; and
   a second inner insulative sheath covering said ventricular conductor, mounted fixedly with respect to said outer sheath.

6. A body implantable lead according to claim 5 wherein said ventricular affixing means further comprising tines.

7. A body implantable lead according to claim 4, 5 or 6 wherein said actively affixing means further comprises:
   a fixation helix having a pointed tip for penetrating body tissue.

8. A body implantable lead according to claim 7 wherein said atrial conductor is rotatable within said outer sheath and wherein said fixation helix is mechanically coupled to said atrial conductor whereby said fixation helix is rotatable by rotation of said atrial conductor.

9. A body implantable lead according to claim 8 wherein said fixation helix is electrically coupled to said atrial conductor.

10. A body implantable lead comprising:
an atrial conductor having a proximal end and a distal end;
a ventricular conductor having a proximal end and a distal end, said ventricular conductor mounted fixedly parallel to said atrial conductor between the proximal end of said atrial conductor and a bifurcation point intermediate the proximal end and the distal end of said atrial conductor wherein said atrial and ventricular conductors diverge distal to said bifurcation point;
an insulative sheath means covering said atrial and ventricular conductors, for maintaining said atrial and ventricular conductors in fixed longitudinal relationship;
a first electrical connector coupled to the proximal end of said atrial conductor;
a second electrical connector coupled to the proximal end of said ventricular conductor;
a ventricular electrode coupled to the distal end of said ventricular conductor; and
an atrial electrode assembly coupled to the distal end of said atrial conductor including active fixation means for maintaining said atrial electrode in contact with body tissue.

11. A body implantable lead according to claim 10 further comprising:
a receiver means fixedly attached to said ventricular conductor at a distance from said bifurcation point equal to the distance from said bifurcation point to said atrial electrode assembly, for removably receiving said active fixation means and for maintaining said atrial conductor generally parallel to said ventricular conductor when said active fixation means is received within said receiver means.

12. A body implantable lead according to claim 11 wherein said receiver means comprises a member having a helical lumen and wherein said active fixation means comprises a rotatable extendable fixation helix insertable in the helical lumen of said receiver means.

13. A body implantable lead according to claim 11 wherein said receiver means is a member formed of a soft, biocompatible material and wherein said active fixation means has a rotatable sharpened helix which may be screwed into said soft biocompatible material.

14. A body implantable lead according to claim 11 or claim 12 or claim 13 wherein said atrial conductor is provided with a bend distal to said bifurcation point.

15. A body implantable lead according to claim 14 wherein said ventricular conductor has a central lumen, and further comprising stylet means for insertion into said central lumen of said ventricular conductor to maintain said ventricular conductor in a generally straight configuration and whereby when said active fixation means is received within said receiving means, said atrial conductor is also maintained in a generally straight configuration.

* * * * *